United States Patent [19]

Tomasso et al.

[11] Patent Number: 5,366,697
[45] Date of Patent: Nov. 22, 1994

[54] TRAY AND MAGNETIC CONVEYOR

[75] Inventors: David A. Tomasso, Rochester;
Johannes J. Porte, Webster; William D. Vanarsdale, Spencerport;
Raymond F. Jakubowicz, Rush;
James D. Riall, Pittsford, all of N.Y.

[73] Assignee: Eastman Kodak Company, Rochester, N.Y.

[21] Appl. No.: 36,800

[22] Filed: Mar. 25, 1993

Related U.S. Application Data

[63] Continuation-in-part of Ser. No. 859,780, Mar. 30, 1992, abandoned.

[51] Int. Cl.⁵ .............................. G01N 35/02
[52] U.S. Cl. ........................ 422/64; 422/63; 422/65; 422/67; 422/58; 211/77
[58] Field of Search ............... 422/63, 64, 65, 67, 422/58; 211/77

[56] References Cited

U.S. PATENT DOCUMENTS

| | | | |
|---|---|---|---|
| 353,554 | 11/1886 | Godfrey | 211/77 |
| 2,144,835 | 1/1939 | Dickinson | 211/1.5 |
| 2,566,430 | 9/1951 | Sobers | 211/77 X |
| 2,609,915 | 9/1952 | De Burgh | 198/41 |
| 2,824,638 | 2/1958 | De Burgh | 198/41 |
| 3,545,933 | 12/1970 | Podschadly et al. | 422/64 X |
| 3,788,816 | 1/1974 | Rohrbaugh et al. | 422/64 X |
| 3,920,502 | 11/1975 | Tokuno | 156/504 |
| 4,052,161 | 10/1977 | Atwood et al. | 422/81 |
| 4,201,286 | 5/1980 | Meier | 198/461 |
| 4,260,581 | 4/1981 | Sakurada | 422/65 |
| 4,301,116 | 11/1981 | Ida et al. | 422/65 |
| 4,322,216 | 3/1982 | Lillig et al. | 23/230 |
| 4,413,534 | 11/1983 | Tomoff et al. | 422/65 |
| 4,795,710 | 1/1989 | Muszak et al. | 422/64 |
| 4,855,110 | 8/1989 | Marker et al. | 422/64 |
| 4,861,554 | 8/1989 | Sakuma | 422/65 |
| 4,892,186 | 1/1990 | Frei | 198/803.01 |
| 4,900,513 | 2/1990 | Barker et al. | 422/64 |
| 5,008,082 | 4/1991 | Shaw | 422/65 |
| 5,080,864 | 1/1992 | Shaw | 422/62 |

FOREIGN PATENT DOCUMENTS 0467301  1/1992  European Pat. Off. .

*Primary Examiner*—James C. Housel
*Assistant Examiner*—Harold Y. Pyon
*Attorney, Agent, or Firm*—Dana M. Schmidt

[57] ABSTRACT

A tray and conveyor for the trays are described, for moving liquid samples in an analyzer. The tray comprises a base having a magnetic member for responding to a magnetic field, a tray frame and member for freely rotatably mounting the frame on the base, the tray frame comprising a plurality of receptacles constructed to receive either sample tubes or aspirating tips useful to aspirate sample from a tube, the receptacles including a fixed bottom support. The conveyor comprises a support, conveying members under the support comprising a plurality of magnets and members for generating a moving magnetic field with the magnets, the conveying members being mounted in a continuous loop under the support and the support being permeable to a magnetic field, one of the above-noted trays being mounted above the support on the base.

8 Claims, 8 Drawing Sheets

TRAY AND MAGNETIC CONVEYOR

RELATED APPLICATIONS

This is a continuation-in-part application of U.S. Ser. No. 859,780 filed on Mar. 30, 1992, now abandoned.

FIELD OF THE INVENTION

This invention relates to trays and conveyors of trays for supplying patient samples to an analyzer.

BACKGROUND OF THE INVENTION

In the field of conveyors, it is known to mount trucks on a solid, impervious flooring under which is provided a magnetic conveyor which causes the trucks to move above the flooring by reason of cooperating magnets mounted under the trucks. Examples are shown, e.g., in U.S. Pat. Nos. 2,609,915 and 2,824,638. However, such trucks have limited capability such as is not particularly useful in a clinical analyzer. That is, they provide fixed horizontal surfaces that lack receptacles needed for sample tubes or pipette tips that have to be carried in an analyzer. Furthermore, they are not capable of rotation on the trucks as is necessary to present multiple positions to a single station. More specifically, they are not freely rotatable on the magnetic base that responds to the magnetic drive underneath.

Therefore, there has been a need for magnetic conveyors that can provide a drive to move a sample tube tray from a loading station to a sample aspiration station, the tray being constructed with receptacles suitable for at least a plurality of sample tubes, and so as to be freely rotatable.

In the field of trays for sample tubes, it is known to provide movable second tube supports that are insertable into the tray above the fixed supports to allow shorter tubes and tubes of varying diameters to be supported by the inserted supports. Examples of such trays are shown, for example, in EPA 467,301 (Doc. 60240). Although such trays function very well, there is a disadvantage: the inserted second supports, when removed from their inserted position, are no longer attached to the tray. As a result, it is possible for the second supports to be lost or misplaced once removed, so that when another second support is required for a particular tray, there is no longer one available. Yet, it is difficult to connect the insertable second supports to the tray without them getting in the way when they are not in use.

Therefore, prior to this invention, there has been a need for a tray that provides a movable second support for tubes above the fixed support, that is permanently connected to the tray without interference, when not in use.

SUMMARY OF THE INVENTION

We have constructed a tray and a conveyor of such trays that solve the above-mentioned problems.

More specifically, in accord with one aspect of the invention, there is provided a sample tube tray for use in a clinical analyzer, the tray comprising a base having magnetic means for responding to a magnetic field, a tray frame and means for freely rotatably mounting the frame on the base, the tray frame comprising a plurality of receptacles constructed to receive either sample tubes or aspirating tips useful to aspirate sample from a tube, the receptacles including a fixed bottom support.

In accord with another aspect of the invention, there is provided a sample tube tray comprising a plurality of receptacles each comprising a fixed bottom support and upper support means above the fixed support for vertically supporting a tube resting on the bottom support, and a movable bottom support for positioning between the fixed support and the upper support means to support a tube of shorter length within the receptacle than is supported by the fixed support. The tray is improved in that the movable support is pivotally attached to the tray, and further including means in the tray defining a recess within the tray adjacent to the pivotal attaching of the tray, for receiving the movable support when it is not in use.

Still another aspect of the invention features a recirculating conveyor of trays for continuously supplying trays to a clinical analyzer, the conveyor comprising a support impermeable to liquid, conveying means under the support comprising a plurality of magnets and means for generating a moving magnetic field with the magnets, the conveying means being mounted along a path under the support and the support being permeable to a magnetic field, and at least one tray mounted above the support and comprising a base having a magnet for cooperating with the magnets of the conveying means, and a frame on the base. The tray further includes means for freely rotatably mounting the frame on the base, the tray frame comprising a plurality of receptacles constructed to receive either sample tubes or aspirating tips useful to aspirate sample from a tube, the receptacles including a fixed bottom support.

Yet another aspect of the invention provides a recirculating conveyor of trays for continuously supplying trays to a clinical analyzer, the conveyor comprising a support impermeable to liquid, conveying means under the support comprising a plurality of magnets and means for generating a moving magnetic field with the magnets, the conveying means being mounted in a continuous loop under the support and the support being permeable to a magnetic field, and at least one tray mounted above the support and comprising a base having a magnet for cooperating with the magnets of the conveying means, and a frame on the base, wherein the tray frame is freely rotatably mounted on the base and further comprises first and second means defining a plurality of vertically extending recesses disposed in first and second concentric rings, respectively, around the frame, the recesses being shaped to receive generally cylindrical articles, the recesses in one ring being of a different size than those in the other ring, the recesses of at least one of the rings each including a fixed bottom support third means defining apertures in the frame, the apertures being vertically aligned with each of the recesses in one of the rings, and a handle on the frame, the handle being concentrically positioned with respect to the rings.

Accordingly, it is an advantageous feature of the invention that a tray is movable by a magnetic conveyor within an analyzer in a way that allows ready access to all parts of the tray, due to its free rotation on its base.

It is another advantageous feature of the invention that such a tray is provided with alternative bottom supports for tubes of varying lengths, which supports are never removed and/or lost from the tray, and are not in the way when not in use.

It is a related advantageous feature of the invention that a cylindrical tray of general utility is provided, that has ready accessibility to tubular articles carried therein.

Other advantageous features will become apparent upon reference to the following Description of the Preferred Embodiments, when read in light of the attached drawings.

DESCRIPTION OF THE PREFERRED EMBODIMENTS

The invention is described hereinafter by references to the preferred embodiments, in which a generally cylindrical tray is used with patient sample tubes and disposable aspirating tips in a clinical analyzer for doing wet assays, the tray having either springs or no springs to hold the tubes from rotating, and, conveying means for the trays that moves the trays in a closed loop. In addition, the invention is useful regardless of the overall shape of the tray or its particular incorporation in an analyzer, and regardless of whether or not springs are used to prevent sample tubes from rotating, or what type of springs are used. It is still further useful whether the conveyor moves the trays in closed loops or open path, and whether the reaction of the analyzer is conducted as a wet assay or as a dry assay.

Directions hereinafter referred to, such as "horizontal", "vertical", "up", "down" and the like refer to orientations that are preferred during the usage of the invention.

Figure 1:
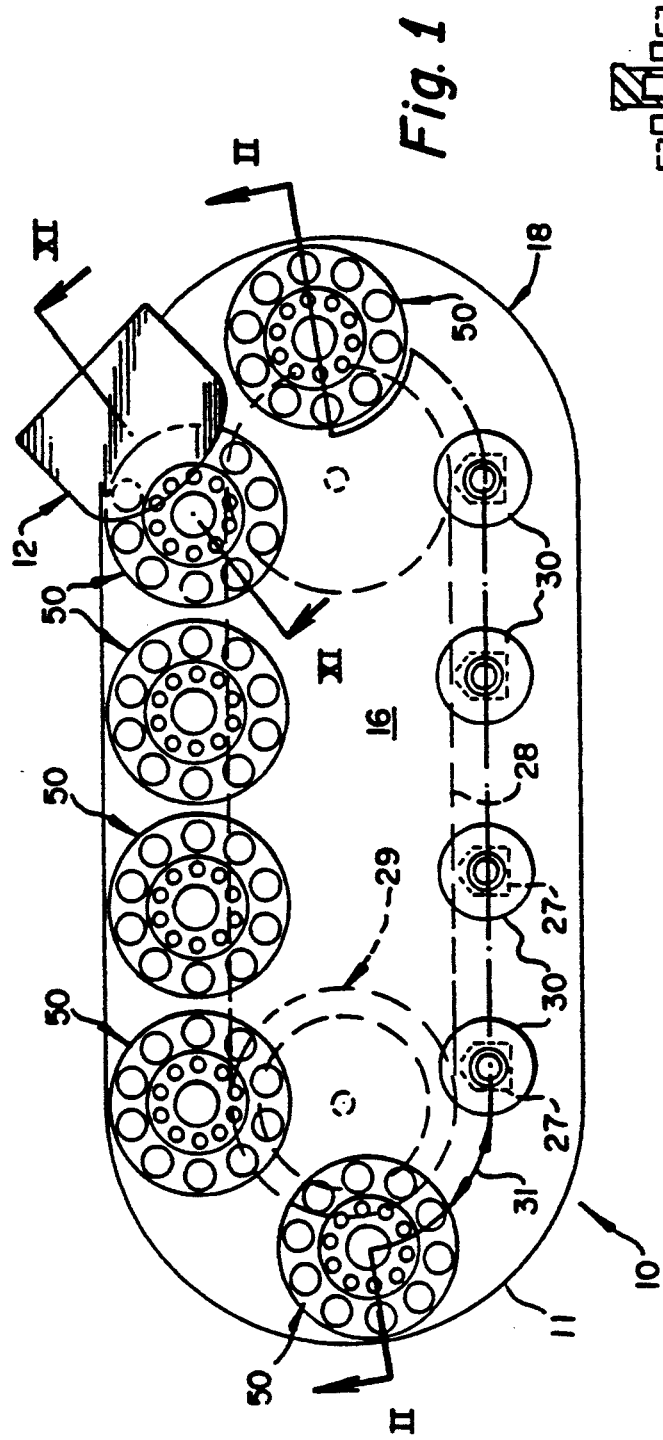
FIG. 1 is a plan view of a conveyor of the invention and aspirating station as they are used in an analyzer.

In accordance with one aspect of the invention, FIG. 1, there is provided a recirculating conveyor 10 of trays 50 for supplying sample-containing tubes to a clinical analyzer, and specifically to an aspirating station 12 of the analyzer. (The details of the aspirator of station 12 are not included, as they can be conventional and do not comprise the invention.) Conveyer 10 in turn includes bases 30 on which trays 50 are removably mounted, and means 14, FIG. 2, for conveying bases 30 and trays thereon around on the top surface 16 of an impermeable support 18, held in place by frame 20 of the analyzer. Most preferably, conveying means 14 comprise a plurality of magnets 22, at least one of the magnets each being held in a housing 24 journalled at 26 in an aperture of a projecting lug 27, FIG. 2, of a continuous belt 28 driven by a suitable pulley 29 and a conventional motor, not shown.

Figure 2:
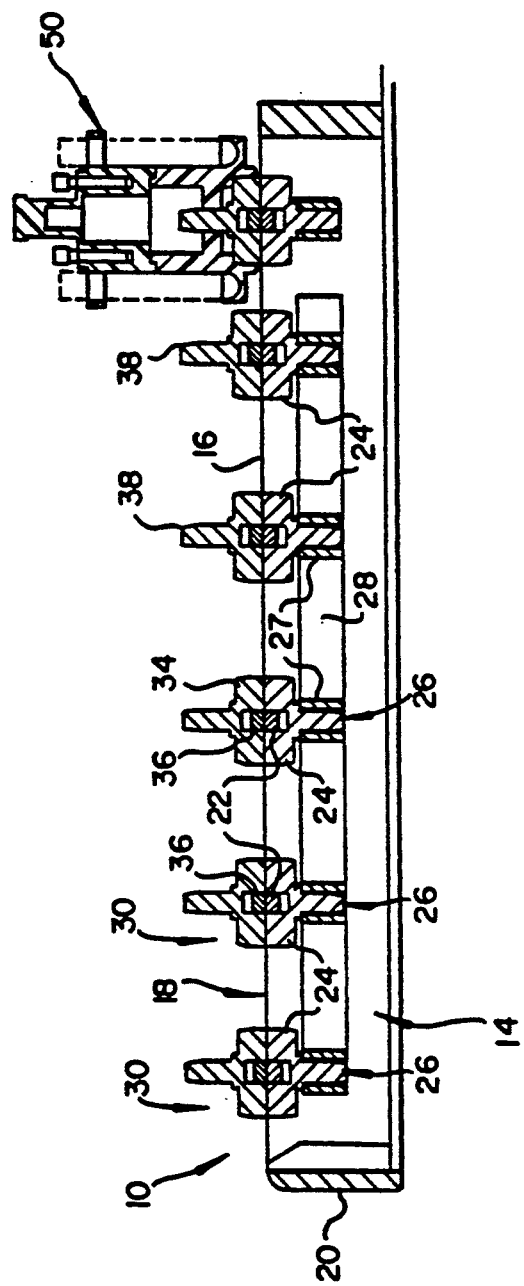
FIG. 2 is a section view taken generally along the line II—II of FIG. 1, with only one tray shown in place.
Figure 3:
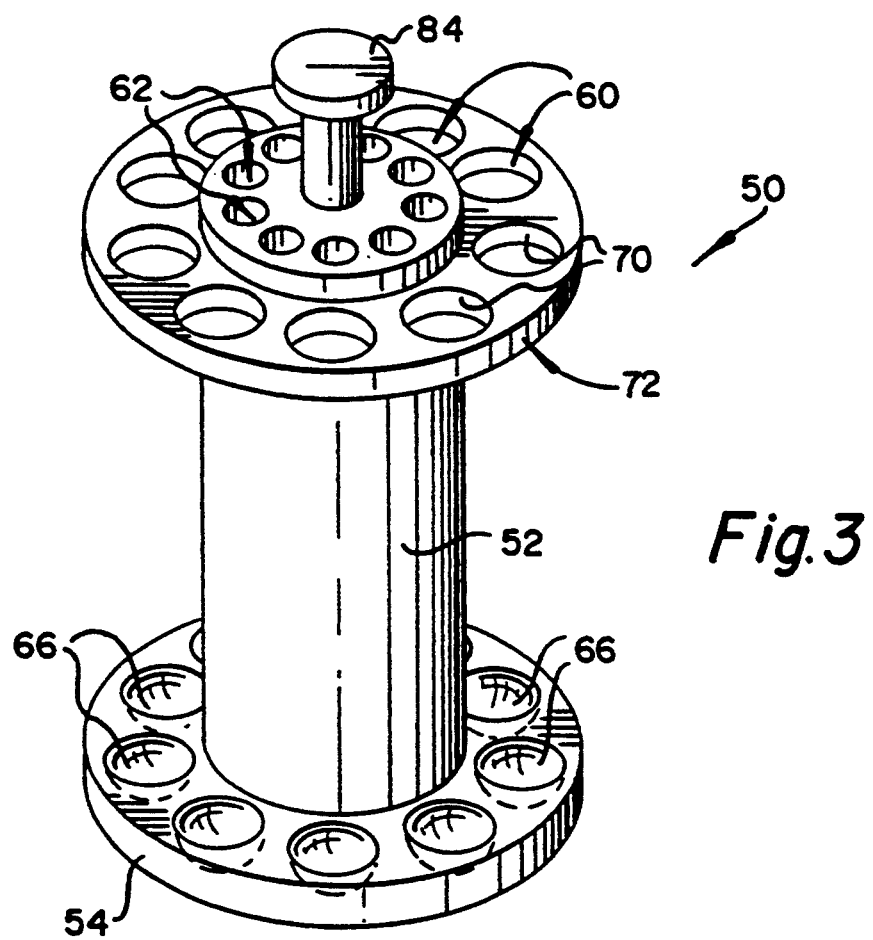
FIG. 3 is an isometric view of a tray constructed in accordance with one aspect of the invention.

Thus there is provided a housing 24, FIG. 2, and at least one magnet 22 to correspond to each base 30. Each housing 24 and base 30 is then caused to circulate around the path 31, FIG. 1, as directed by belt 28, which can be any desired path, on top of surface 16. The advantage of such a conveying means is, of course, that liquids spilled, if any, out of the trays will fall only onto surface 16 and not into the conveying mechanism, thus simplifying cleaning. End 11 of conveyor 10 is used to manually remove used trays and to add new ones with new sample tubes. Alternatively, robotic loading & unloading can be used.

Bases 30 in turn comprise a housing 34 which can be similar or identical to housings 24, in which at least one magnet 36 is placed to magnetically interact with magnets 22 of housings 24. Each housing 34 has a spindle 38 which can be identical to the spindles by which housings 24 are journalled at 26 into lugs 27. The center of each spindle defines an axis of rotation as will become apparent.

Figure 4:
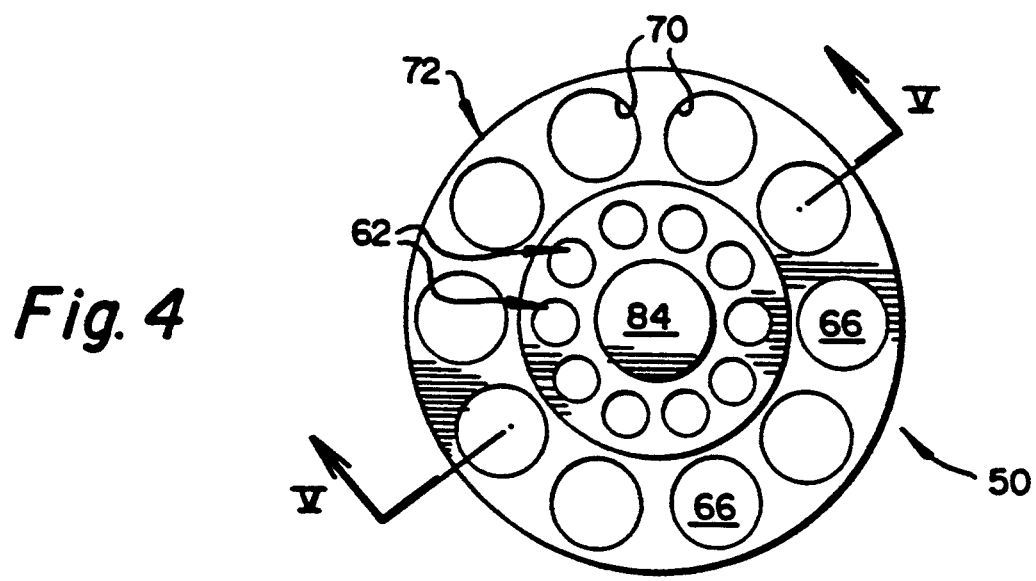
FIG. 4 is a plan view of the tray of FIG. 3.

In accordance with another aspect of the invention, trays 50 are removably and rotatably mounted on bases 30, and specifically preferably to rotate concentrically about spindles 38. As shown more clearly in FIGS. 3-6, such a tray comprises a frame 52 having a bottom portion 54 recessed at 56 and 58 to receive housing 34 and spindle 38, respectively, FIG. 5. Frame 52 further comprises a plurality of receptacles 60 and 62 to receive conventional sample tubes T and conventional aspirating tips t, respectively, where tubes T can be of varying sizes. Receptacles 60 preferably comprise bottom portion 54 providing a fixed bottom support having therein fixed sockets 66 formed as cylindrical recesses, and directly vertically above the sockets, means 70 defining circular apertures. Preferably, a ring 72 extends out over support 64 and sockets 66, FIG. 4, to provide an upper support for tubes T, since it is in this ring 72 that apertures 70 are formed, most preferably so as to be vertically aligned with sockets 66. The internal diameters of sockets 66 and apertures 70 are such as to accommodate the largest tubes T of sample that are to be used.

Apertures 70 are shown as formed by a complete closure in ring 72. Optionally, however, a small gap in the closure is tolerable, provided it is not large enough to allow a tube to fall out.

On the other hand, receptacles 62 can be simple cylindrical bores extending preferably vertically down into frame 52, of a size and shape to hold tips t therein by their fins. Receptacles 62 thus preferably form a concentric ring that is preferably inside the concentric ring formed by receptacles 60, although the ring of receptacles 62 can also be outside the ring of receptacles 60 if ring 72 is extended considerably farther from axis 80, the axis of symmetry of tray 50.

Figure 5:
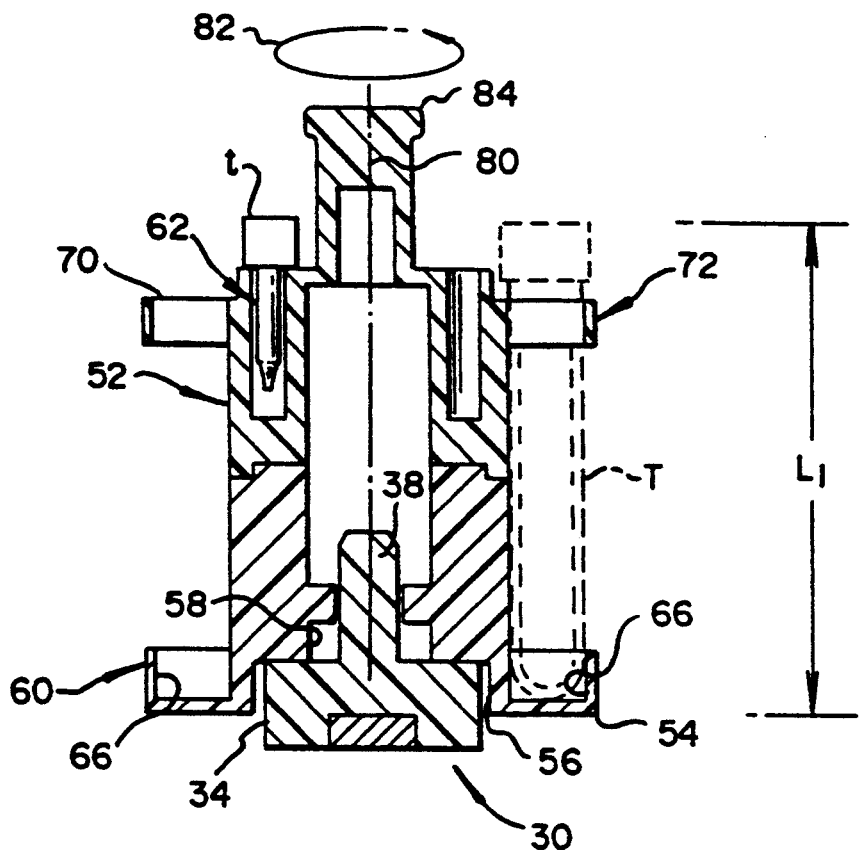
FIG. 5, is a section view taken along the lines V—V of FIG. 4.

Axis 80 is also preferably the axis of rotation arrow 82, of tray 50, FIG. 5. Such rotation can be achieved manually, for example, by using handle 84 that is mounted preferably on axis 80. Preferably, it is rotated mechanically by means hereinafter described.

Figure 6:
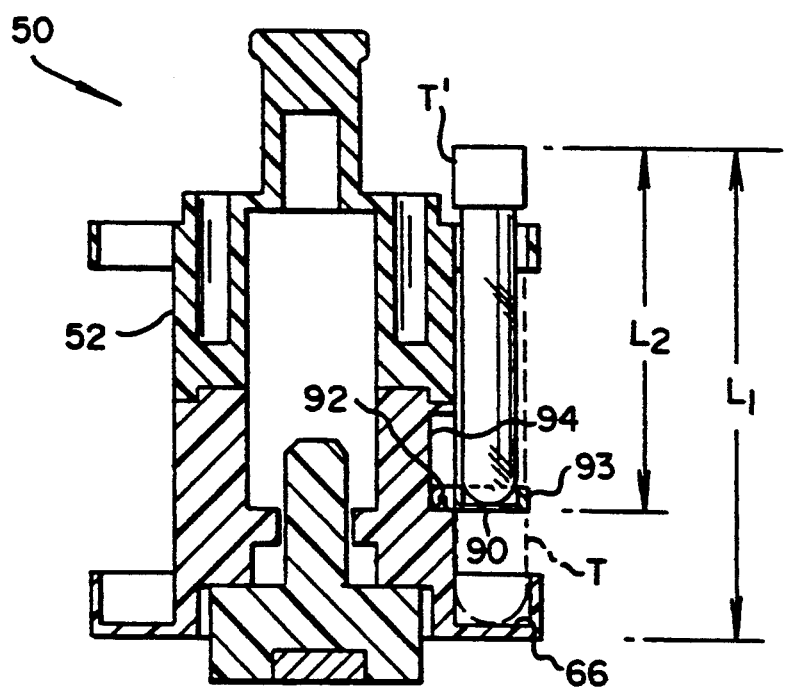
FIG. 6 is a section view similar to that of FIG. 5, illustrating an alternate embodiment.

Tips t need not have more than one size. However, tubes T conventionally come also in sizes smaller than the length $L_1$ shown in FIG. 5. For example, length $L_2$ is also common, with or without the same diameter for tube T', FIG. 6. In accordance with another aspect of the invention, trays 50 can include a second, moveable bottom support 90 for such shorter tubes, and means 92 for pivotally and permanently mounting supports 90 on frame 52 between the fixed bottom support of portion 54 and the upper support of ring 70. Support 90 includes a vertically extending shoulder 93, which can be a partial ring, or a complete ring (as shown) to act as a socket for supporting tube T'. Such an arrangement permits movable supports 90 to pivot into or out of alignment with apertures 70 (and the bottom support of sockets 66), to allow either a tube T' of length $L_2$ or tube T of length $L_1$, respectively, to be supported. At the same time, support 90 remains attached at all times to frame 52, even when not in active use. As shown in FIG. 6, pivot means 92 comprise pins that permit pivoting of movable supports 90 about a horizontal axis.

Additionally, there is preferably included a recess 94 for each support 90, in tray frame 52, shaped to receive support 90 when it is pivoted out of the way to allow a tube T of length $L_1$ to be supported and carried. Recess 94 is of course adjacent to pin 92, and is sufficiently deep as to accommodate support 90 generally flush with the vertical sidewall of frame 52, when support 90 is pivoted out of the way.

Alternatively, the movable support can be pivoted about a vertical axis, so that the support moves within a horizontal plane, FIGS. 7–10. Parts similar to those previously described bear the same reference numeral to which the distinguishing suffix "A" is appended.

Figure 7:
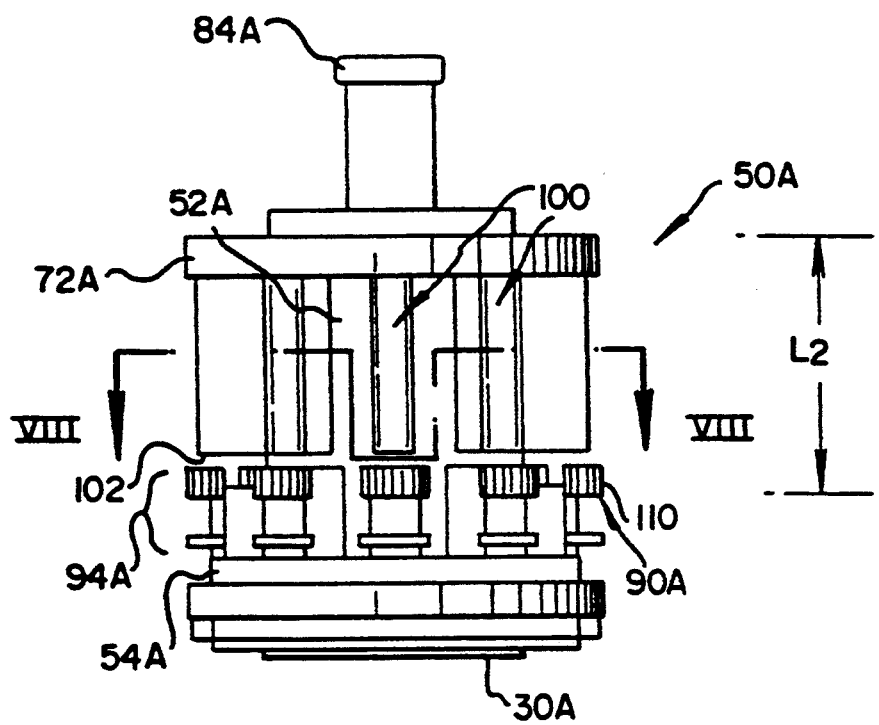
FIG. 7 is a side elevational view of a tray showing yet another alternate embodiment.
Figure 8:
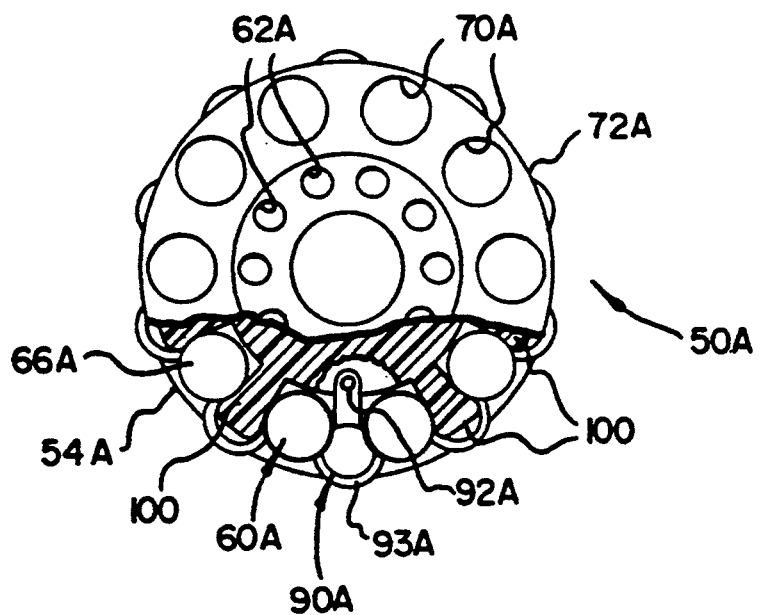
FIGS. 8 & 9 are fragmentary section views taken generally along the line VIII—VIII of FIG. 7, showing different positions of the second bottom support.
Figure 9:
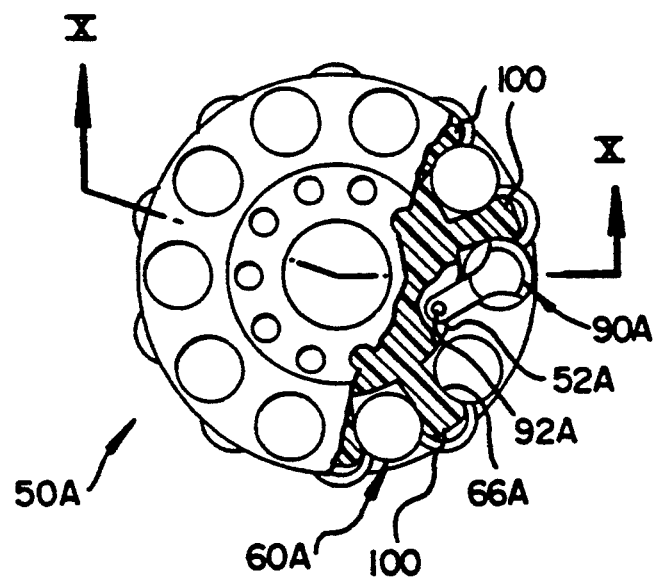
Figure 10:
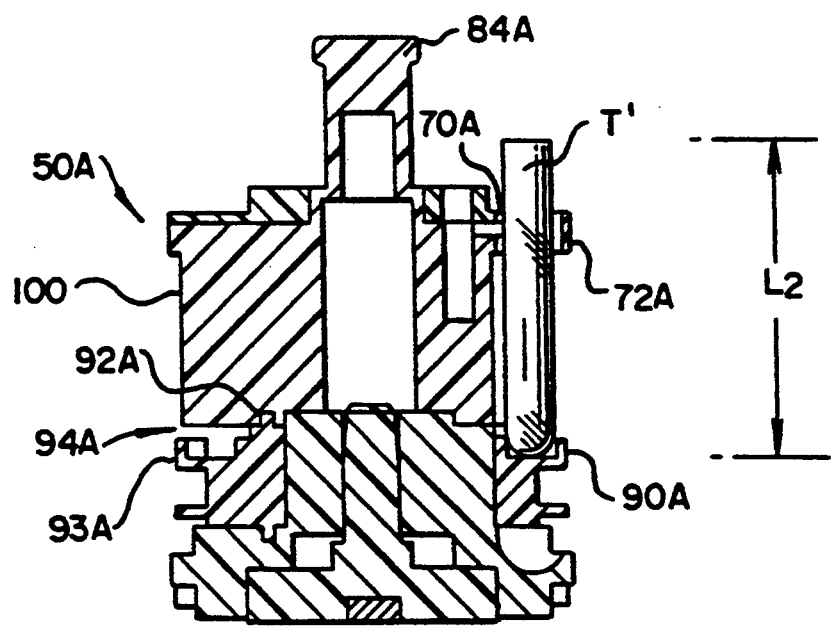
FIG. 10 is a section view taken along the line X—X of FIG. 9, showing the gearing engagement at the aspiration station.

Thus, FIGS. 7–8, tray 50A sits on a base 30A, FIG. 7, and comprises a frame 52A with a fixed bottom support 54A in which recessed sockets 66A are formed, FIG. 8, upper ring 72A with apertures 70A to complete, with sockets 66A, receptacles 60A, bores 62A, for tips t (not shown), and handle 84A as described heretofore, FIG. 7.

Additionally, to facilitate manual grasping of tray 50A at other than handle 84A, frame 52A includes as part of the vertical support of tubes T or T', fixed ribs 100, FIGS. 7 and 8, that project outwardly between receptacles 60A, as part of frame 52A, FIG. 8. Ribs 100 are removed, however, at the portion 102, FIG. 7, adjacent bottom support 54A, to create recesses 94A within which movable bottom supports 90A are pivotally mounted by pins 92A, FIG. 8, that are disposed vertically for horizontal pivoting. At least a portion of shoulder 93A is provided in supports 90A, to assist in seating a shorter tube of length $L_2$, FIG. 7.

Optionally, exterior portions of supports 90A can be knurled, as at 110, for example, to provide easier manual grasping of the movable supports.

As shown in FIGS. 7 and 8, supports 90A are withdrawn into their recesses 94A, so that the largest tube can be inserted into receptacles 60A. However, when a tube T' is to be used, FIGS. 9 and 10, a support 90A is pivoted within a horizontal plane out of its recess 94A, FIG. 10, and into vertical alignment with an aperture 70A, to act as the bottom support for tube T' of a length $L_2$. This is easily done by the operator of the analyzer, when the tray is removed from its base 30A via handle 84A to manually load sample tubes into receptacles 60A.

Figure 11:
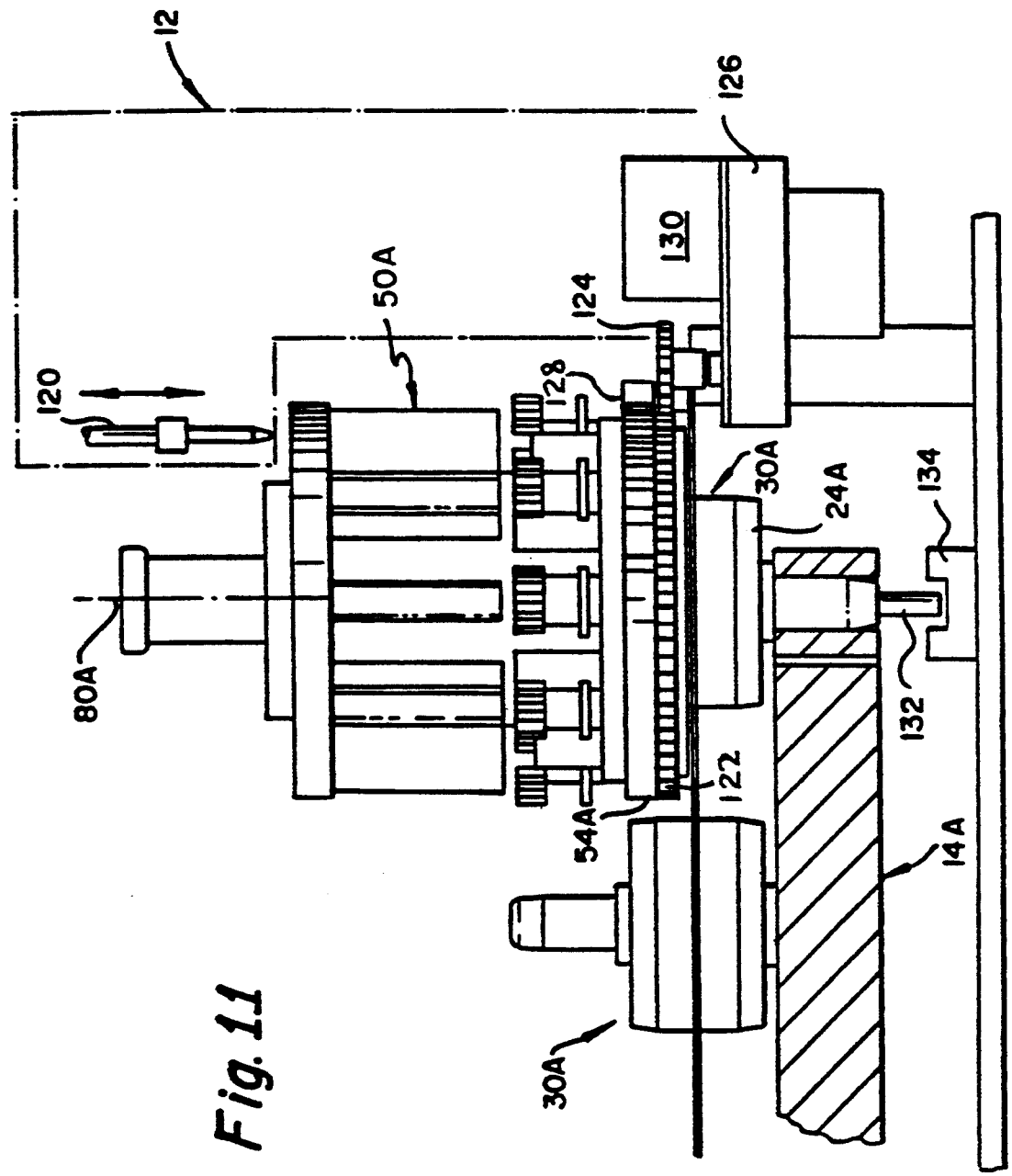
FIG. 11 is a fragmentary elevational view in section, taken along line XI—XI of FIG. 1.

As noted above, the function of conveyor 10 is to move trays 50 or 50A into position at aspirator station 12, which includes a conventional aspirator 120, FIG. 11. However, because of the free rotation of trays 50A on base 30A about axis 80A, it is important that tray 50A be rotated somehow to place the desired sample tube directly under aspirator 120. To this end, means such as a gear 122 are mounted around the circumference of bottom portion 54A, for engagement by a suitable drive means, such as a pinion gear 124 driven by motor 126. Conveying means 14A is effective to force gear 122 into engagement with gear 124, which is preferably already rotating as a tray approaches the aspirating station. The magnetic coupling of each tray to conveying housings 24A is sufficiently compliant to accommodate any inadvertent misalignment of gear teeth at the time of meshing. A signalling means in turn is used to designate at least a "home" position, and to this end any flag 128, e.g., a projecting shoulder, a magnet, or a light reflector is disposed on frame 52A, e.g., adjacent bottom portion 54A. The flag cooperates with a signal generator 130, which comprises either an extending trigger switch (not shown) that triggers when contacted by the shoulder of the flag, or a cooperating magnet or coil to respond to the magnet of the flag, or a photoelectric emitter and detector pair that cooperate with the reflector of the flag.

Optionally, one of the housings 24A can include a flag 132 depending therefrom, which cooperates with signal generator 134 to identify which tray is the "home" tray on the conveying means.

Figure 12:
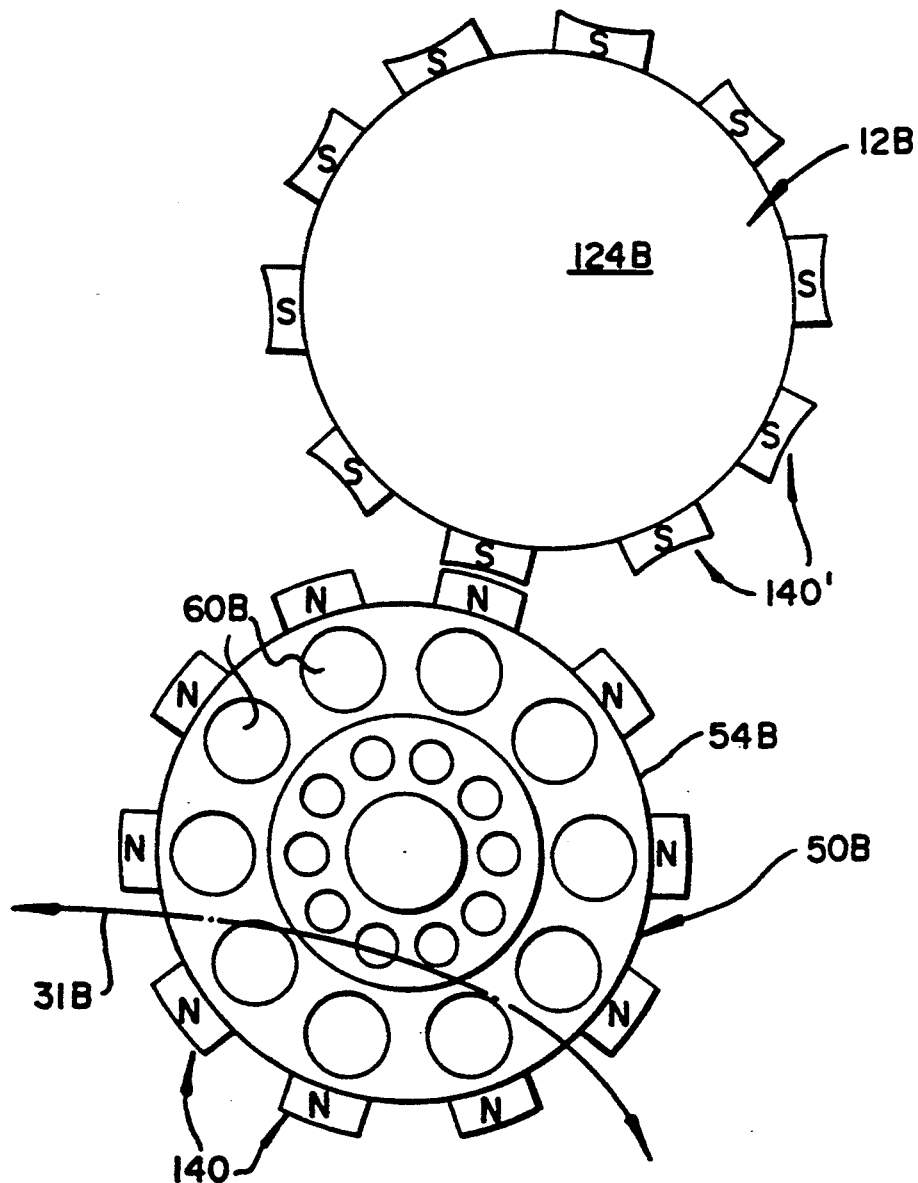
FIG. 12 is a fragmentary plan view of a tray on the conveyor and of an alternative rotating means for controlling the rotation of a tray at an aspirating station.

Alternatively, FIG. 12, the means for rotating tray 50 or 50A can comprise, for example, devices other than gears. Parts similar to those previously described bear the same reference numeral, to which the distinguishing suffix "B" is appended. Thus, tray 50B is as described for either of the two embodiments above, with receptacles 60B for sample tubes, rotatably mounted on a base, not shown. Aspirator station 12B is positioned adjacent to the closed path 31B traced by trays 50B, also as described above. However, the controlled and directed rotation of a tray, to align receptacles 60B with the aspirator of station 12B, comprises paired north and south magnets 140, 140' disposed around bottom portion 54B, and on a drive wheel 124B. A "home" signalling means such as is described above, is also used to identify which receptacle is under the aspirator.

Figure 13:
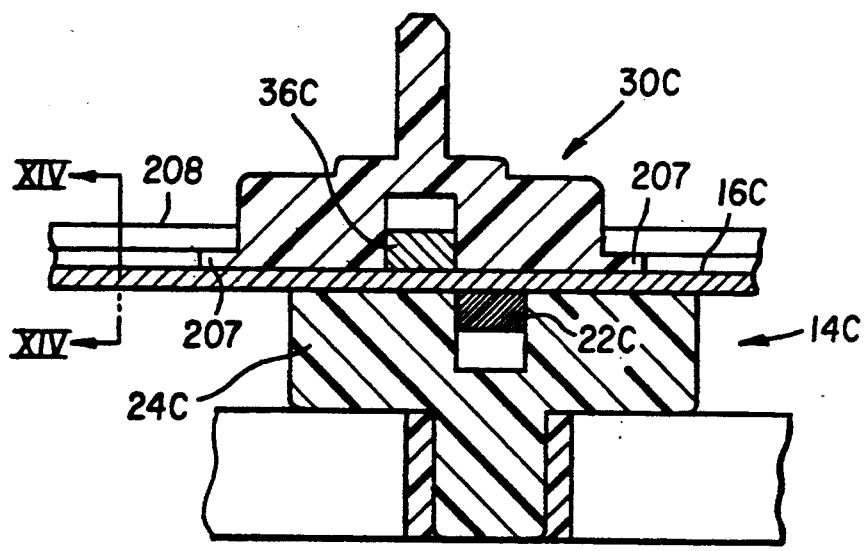
FIG. 13 is a fragmentary elevational view in section, similar to FIG. 2 but enlarged, of an alternate embodiment of the invention.
Figure 14:
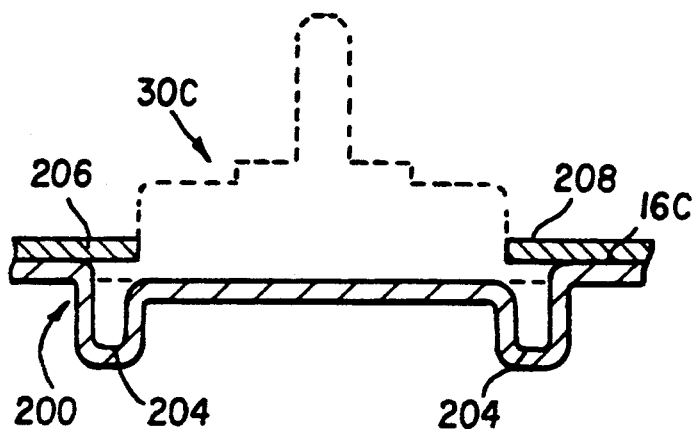
FIG. 14 is a section view taken generally along the line XIV—XIV of FIG. 13.
Figure 15:
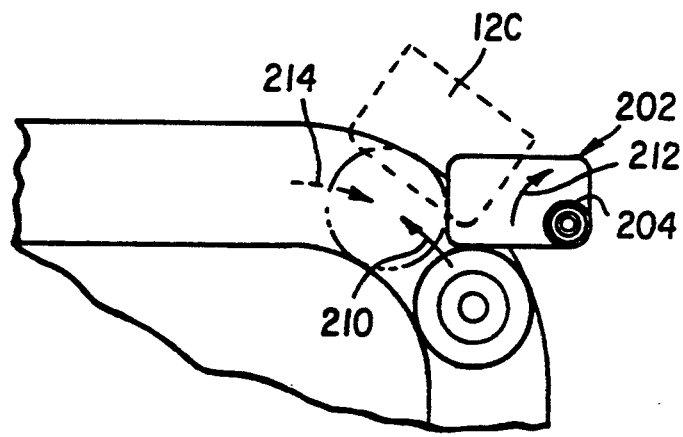
FIG. 15 is a fragmentary plan view similar to FIG. 1, but of the alternate embodiment of FIG. 13.

The interaction of the magnets 22 and 36 shown in FIG. 2 shows one of attraction. In the alternative, it can be one of repulsion so as to minimize the force that has to be delivered by belt 28 to move the trays over surface 16, as shown in FIGS. 13 and 14. Parts similar to those previously described bear the same reference numerals to which the distinguishing suffix "C" is appended. Thus, bases 30C and conveying means 14C are constructed as before, except that magnets 22C and 36C are arranged to be repulsive, forcing the base 30C to move in advance of the underlying housing 24C. Also, since a repulsive force can be omnidirectional, it is preferred that surface 16C be shaped, FIG. 14, with a track 200 to guide the bases. The track preferably has a general W-shape in section. Most preferably, FIG. 14, a gutter is provided at each edge 204 between which the surface 16C is disposed between the level of the gutters and the surface 16C elsewhere, to retain the bases 30C. That is, the gutters tend to collect any spilled liquid, for cleaning. Overhangs 206 and 208 are provided above each edge 204 to cooperate with a lip 207 on bases 30C, FIG. 13, to restrain those bases from magnetically "jumping" vertically out of alignment, in the event the respective housing for such a base is inadvertently forced directly underneath the base. To assist in cleaning out at least one of the gutters, overhang 206, FIG. 14, can be removably attached rather than permanently attached.

In such an arrangement, there is a need for a positive stop of the tray at station 12C, and accordingly a pivotable stop member 202 is mounted adjacent station 12C, with a spring 204 biasing it outwardly into the track. As a tray comes by, arrow 210, the member 202 pivots out of the way, arrow 212. The conveyor is then reversed enough, dotted arrow 214, until the tray abuts against the member 202 as shown in phantom.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A recirculating mechanism for continuously supplying trays to a clinical analyzer, said mechanism comprising a support impermeable to liquid, a conveyor under said support comprising a plurality of magnets and means for generating a moving magnetic field with said magnets, said conveyor being mounted along a recirculating path under said support and said support being permeable to a magnetic field, and at least one tray mounted above said support and comprising a base having a magnet for cooperating with said magnets of said conveyor, and a frame on said base, said tray further including means for freely rotatably mounting said frame on said base, and said tray frame comprising a plurality of receptacles constructed to receive either sample tubes or aspirating tips useful to aspirate sample from a tube, said receptacles including a fixed bottom support.

2. A recirculating mechanism for continuously supplying trays to a clinical analyzer, said mechanism comprising a support impermeable to liquid, a conveyor under said support comprising a plurality of magnets and means for generating a moving magnetic field with said magnets, said conveyor being mounted in a continuous loop under said support and said support being permeable to a magnetic field, and at least one tray mounted above said support and comprising a base having a magnet for cooperating with said magnets of said conveyor, and a frame on said base, said frame being freely rotatably mounted on said base and further comprising first and second means defining a plurality of vertically extending recesses disposed in first and second concentric rings, respectively, around said frame, said recesses being shaped to receive generally cylindrical articles, the recesses in one ring being of a different size than those in the other ring, the recesses of at least one of said rings each including a fixed bottom support, third means defining apertures in said frame, said apertures being vertically aligned with each of said recesses in one of said rings, and a handle on said frame, said handle being concentrically positioned with respect to said rings.

3. A mechanism as defined in claims 1 or 2, and further including rotating means at an aspirating station for rotating said tray on said base.

4. A mechanism as defined in claim 3, wherein said rotating means comprise gear means on said frame and an engaging driving gear at an aspirating station, said conveyor being constructed to hold said gear and said gear means in engagement at said aspirating station.

5. A mechanism as defined in claim 4, and further including signalling means for signalling the position on the frame that is engaged by said driving gear.

6. A mechanism as defined in claim 1 or 2, and further including a movable support pivotally mounted on said frame for movement into and out of position above at least some of said fixed supports, so that cylindrical sample tubes of different lengths can be carried by said tray.

7. A mechanism as defined in claim 1 or 2, wherein said magnets of said trays are attracted by the magnets of said conveyor.

8. A mechanism as defined in claim 1 or 2, wherein said magnets of said trays are repelled by the magnets of said conveyor means.

* * * * *